United States Patent [19]

Doi et al.

[11] Patent Number: 5,384,228
[45] Date of Patent: Jan. 24, 1995

[54] ALKALI-DEVELOPABLE POSITIVE-WORKING PHOTOSENSITIVE RESIN COMPOSITION

[75] Inventors: Kousuke Doi; Satoshi Niikura, both of Samukawa; Nobuo Tokutake; Hidekatsu Kohara, both of Chigasaki; Toshimasa Nakayama, Chigasaki, all of Japan

[73] Assignee: Tokyo Ohka Kogyo Co., Ltd., Kanagawa, Japan

[21] Appl. No.: 134,287

[22] Filed: Oct. 8, 1993

Related U.S. Application Data

[63] Continuation-in-part of Ser. No. 46,230, Apr. 13, 1993, abandoned.

[30] Foreign Application Priority Data

Apr. 14, 1992 [JP] Japan .................. 4-119571

[51] Int. Cl.[6] .................. G03F 7/023; G03F 7/30
[52] U.S. Cl. .................. 430/192; 430/165; 430/191; 430/193; 534/557
[58] Field of Search .............. 430/191, 192, 193, 165; 534/557

[56] References Cited

U.S. PATENT DOCUMENTS

| | | | |
|---|---|---|---|
| 3,046,118 | 7/1962 | Schmidt et al. | 96/33 |
| 3,106,465 | 10/1963 | Neugebauer et al. | 96/33 |
| 3,148,983 | 9/1964 | Endermann et al. | 96/33 |
| 3,188,210 | 6/1965 | Fritz et al. | 430/193 |
| 4,738,915 | 4/1988 | Komine et al. | 430/191 |
| 5,110,706 | 5/1992 | Yumoto et al. | 430/192 |
| 5,112,719 | 5/1992 | Yamada et al. | 430/192 |
| 5,153,096 | 10/1992 | Uenishi | 430/165 |
| 5,173,389 | 12/1992 | Uenishi et al. | 430/190 |
| 5,208,138 | 5/1993 | Lazarus et al. | 430/192 |
| 5,238,775 | 8/1993 | Kajita et al. | 430/190 |
| 5,290,658 | 3/1994 | Uenishi et al. | 430/192 |
| 5,306,596 | 4/1994 | Oie et al. | 430/192 |

FOREIGN PATENT DOCUMENTS

| | | |
|---|---|---|
| 3718015 | 8/1959 | Japan . |
| 6228457 | 6/1962 | Japan . |
| 57-34122 | 2/1982 | Japan . |
| 211618 | 1/1990 | Japan . |
| 2300751 | 12/1990 | Japan . |
| 2300752 | 12/1990 | Japan . |
| 348249 | 3/1991 | Japan . |
| 3158856 | 7/1991 | Japan . |
| 436751 | 2/1992 | Japan . |

*Primary Examiner*—Charles L. Bowers, Jr.
*Assistant Examiner*—John S. Chu
*Attorney, Agent, or Firm*—Henry T. Burke

[57] ABSTRACT

A novel alkali-developable photosensitive resin composition, which is suitable for use as a photoresist composition for fine patterning in the manufacture of various electronic devices, is proposed. The photosensitive resin composition comprises, as the essential ingredients, (a) an alkali-soluble novolac resin as the film-forming ingredient and (b) a very specific compound which is a 1,2-quinone diazide sulfonic acid ester of a condensation product having a weight-average molecular weight of 400 to 2000 obtained by the condensation reaction between phenol and a hydroxybenzaldehyde in the presence of an acidic catalyst as the photosensitizing agent. By virtue of the formulation with this specific photosensitizer, the resist layer formed from the inventive composition has a greatly increased focusing latitude in addition to the excellent sensitivity, resolution and heat resistance.

7 Claims, No Drawings

ALKALI-DEVELOPABLE POSITIVE-WORKING PHOTOSENSITIVE RESIN COMPOSITION

BACKGROUND OF THE INVENTION

This is a continuation-in-part application from a co-pending U.S. patent application Ser. No. 08/046,230 filed Apr. 13, 1993, now abandoned.

The present invention relates to an alkali-developable positive-working photosensitive resin composition which can be used satisfactorily as a resist for ultrafine patterning works in the manufacture of various kinds of semiconductor devices such as ICs, LSIs and the like.

As is well known, the manufacturing process of various kinds of semiconductor devices such as ICs, LSIs and the like involves a photolithographic fine patterning process in which a semiconductor silicon wafer is provided on the surface with a thin layer of a photoresist composition which is exposed pattern-wise to ultraviolet light through a photomask bearing the pattern for the desired semiconductor device to form a latent image of the pattern followed by development of the pattern by using a developer solution to give a patterned resist layer which serves to protect the substrate surface in the subsequent working of etching and the like.

As the photoresist composition used in this photolithographic method, the compositions most widely used are those by the formulation comprising an alkali-soluble novolac resin as a film-forming ingredient and a photosensitizer which is typically a compound having a quinone diazide group in the molecule or, in particular, a naphthoquinone-1,2-diazide sulfonic acid ester of an aromatic polyhydroxy compound. When a photoresist composition of still higher sensitivity is desired, it is usual to use a photosensitizer of which the aromatic polyhydroxy compound is selected from gallic acid esters and polyhydroxy benzophenone compounds. Particular examples of the naphthoquinone-1,2-diazide sulfonic acid ester of a polyhydroxy benzophenone include those disclosed in U.S. Pat. Nos. 3,046,118, No. 3,106,465 and No. 3,148,983 and Japanese Patent Publications No. 37-18015 and No. 62-28457.

In order to comply with the trend of recent years in the field of manufacture of semiconductor devices toward more and more increasing fineness of working, photoresist compositions are also required to have further enhanced sensitivity in pattern-wise exposure to light and to be capable of giving a higher contrast of the patterned images as well as to have further improved heat resistance to withstand the conditions encountered in dry etching or other treatment.

As a photoresist composition to satisfy the above mentioned requirements, proposals have been made in Japanese Patent Kokai No. 1-189644 for a positive-working photoresist composition of which the photosensitizer ingredient is a naphthoquinone-1,2-diazide sulfonic acid ester of a specific trihydroxy triphenyl methane compound and in Japanese Patent Kokai No. 4-36751 for a positive-working photoresist composition of which the photosensitizer ingredient is a naphthoquinone-1,2-diazide sulfonic acid ester of 1-[1-(4-hydroxyphenyl) isopropyl]-4-[1,1-bis(4-hydroxyphenyl) ethyl] benzene.

Although these photoresist compositions mentioned above can satisfy the requirements for the sensitivity, resolution and heat resistance to some extent, photoresist compositions in recent years are required to be further upgraded in respect of the focusing latitude so that highest accuracy and precision can be maintained in the fine patterning of the resist layer to comply with the changes in the depth of focus due to the difference in the thickness of the photosensitive layer in the pattern-wise exposure to light.

SUMMARY OF THE INVENTION

The present invention accordingly has an object to provide a positive-working photosensitive resin composition suitable for use as a photoresist in ultrafine patterning works having a greatly increased focusing latitude in addition to excellent sensitivity, resolution and heat resistance.

Thus, the present invention provides an alkali-developable positive-working photosensitive resin composition which comprises, as a uniform blend:

(a) an alkali-soluble novolac resin;
(b) a 1,2-quinone diazide sulfonic acid ester of a condensation product having a weight-average molecular weight in the range from 400 to 2000 obtained by the condensation reaction between phenol and a hydroxybenzaldehyde in the presence of an acidic catalyst; and
(c) though optional, an aromatic compound represented by the general formula

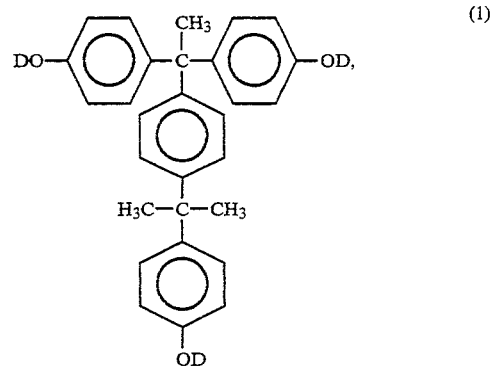

in which at least one of the groups denoted by D is a naphthoquinone-1,2-diazide-sulfonyl group, the remainder, if any, of the groups denoted by D being each a hydrogen atom.

The amount of the component (b) in the inventive composition is in the range from 5 to 200 parts by weight per 100 parts by weight of the component (a). The amount of the component (c), when used, is in such a range that the total amount of the components (b) and (c) is in the range from 5 to 200 parts by weight per 100 parts by weight of the component (a).

DETAILED DESCRIPTION OF THE PREFERRED EMBODIMENTS

As is described above, the essential ingredients in the inventive alkali-developable positive-working photosensitive resin composition are the alkali-soluble novolac resin as the component (a) which is a film-forming agent and the specific compound as the component (b) which is a photosensitizer. The inventive photosensitive resin composition gives a photoresist having a very large focusing latitude along with excellent sensitivity, resolution and heat resistance. The advantages obtained by the inventive photosensitive resin composition can further be enhanced by compounding the composition additionally with a second photosensitizing compound as the component (c).

The alkali-soluble novolac resin as the component (a) in the inventive composition is not particularly limitative and can be selected from any alkali-soluble novolac resins conventionally used as a film-forming agent in the positive-working photoresist compositions of the prior art. Examples of suitable novolac resins include those obtained by the condensation reaction between an aromatic hydroxy compound or phenolic compound such as phenol, cresol, xylenol and the like with an aldehyde compound such as formaldehyde in the presence of an acidic catalyst. Preferably, the alkali-soluble novolac resin used in the inventive composition has a weight-average molecular weight in the range from 2000 to 20000 or, more preferably, from 5000 to 15000 after removal of the fractions of lower molecular weight by fractional precipitation in respect of the higher heat resistance of the photoresist prepared from the composition.

The essential photosensitizing compound as the component (b) is a 1,2-quinone diazide sulfonic acid ester of a condensation product having a weight-average molecular weight in the range from 400 to 2000 obtained by the condensation reaction between phenol and a hydroxybenzaldehyde in the presence of an acidic catalyst. This compound can be prepared by the full or partial esterification reaction of a condensation product between phenol and hydroxybenzaldehyde with a 1,2-diazide sulfonyl halide in an organic solvent such as dioxane, dimethylacetamide, dimethylformamide and the like in the presence of an alkaline or basic compound such as triethanolamine, triethylamine, alkali carbonates, alkali hydrogencarbonates and the like.

The above mentioned condensation product between phenol and a hydroxybenzaldehyde can be prepared by the dehydration condensation reaction between phenol and a hydroxybenzaldehyde in the presence of an acidic catalyst according to the method disclosed in Japanese Patent Kokai No. 57-34122 and No. 2-11618. Any of o-, m- and p-hydroxybenzaladehydes can be used for the purpose but o-hydroxybenzaldehyde is preferred. Examples of suitable acidic catalyst compounds include those conventionally used in the condensation reaction between a phenolic compound and an aldehyde for the preparation of a novolac resin such as hydrochloric acid, sulfuric acid and other inorganic acids and oxalic acid, toluene sulfonic acid and other organic acids. It is known that the condensation reaction takes place between the aldehyde carbon of the hydroxybenzaldehyde and the ortho- and/or para-positions of the phenol relative to the phenolic hydroxy group.

It is essential that the condensation product used as the reactant in the above mentioned esterification reaction has a weight-average molecular weight in the range from 400 to 2000 or, preferably, from 500 to 1300 with reference to polystyrenes. When the average molecular weight of the condensation product is too large, disadvantages are caused in respect of the sensitivity, resolution and focusing latitude of the photosensitive resin composition while, when the molecular weight thereof is too small, the photoresist layer after patterning would have somewhat decreased heat resistance. The component (b) can be a combination of two kinds or more of different compounds each in conformity with the definition according to need.

The second photosensitizing compound as the component (c) represented by the general formula (I) is used optionally in combination with the component (b) with an object to further improve the focusing latitude in the pattern-wise exposure of the resist layer to light and the resolution of the patterned resist layer. This is a known compound disclosed, for example, in Japanese Patent Kokai No. 3-48249 and No. 4-36751 and can be prepared, for example, by the full or partial esterification of 1-[1-(4-hydroxyphenyl) isopropyl]-4-[1,1-bis(4-hydroxyphenyl) ethyl] benzene with a naphthoquinone-1,2-diazide-sulfonyl halide in a polar organic solvent such as dioxane, dimethylacetamide, dimethylformamide and the like in the presence of an alkali or a basic compound such as triethanolamine, triethylamine, alkali carbonates, alkali hydrogen carbonates and the like as an acid acceptor.

Satisfactory results can be obtained in the esterification reaction for the preparation of the components (b) and (c) by using naphthoquinone-1,2-diazide-4-sulfonyl chloride or naphthoquinone-1,2-diazide-5-sulfonyl chloride as the naphthoquinone-1,2-diazide-sulfonyl halide.

The components (b) and (c) each can be either a single compound or a combination of two or more compounds within the definition of the respective components.

The amount of the photosensitizer ingredient, i.e. the component (b) or a combination of the components (b) and (c), in the inventive photosensitive resin composition is in the range from 5 to 200 parts by weight per 100 parts by weight of the component (a). When the amount thereof is too small, a patterned resist layer having high fidelity of the reproduced images can hardly be obtained from the resin composition while, when the amount thereof is too large, on the other hand, uniformity of the resist layer is decreased along with a decrease in the resolution of the patterned images. When the components (b) and (c) are used in combination, the weight proportion of the component (b) to the component (c) is in the range from 1:10 to 10:1 or, preferably, in the range from 3:7 to 7:3. When the weight proportion of the component (c) is too small, the focusing latitude and resolution cannot be sufficiently improved while, when the weight proportion of the component (c) is too large, the advantage to be obtained by the use of the component (b), i.e. improvement in the heat resistance of the resist layer can hardly be obtained.

It is optional according to need that the photosensitive resin composition of the invention is further admixed with a condensation product of a sulfonyl chloride of other quinone diazide group-containing compounds such as orthobenzoquinone diazide, orthonaphthoquinone diazide, orthoanthraquinone diazide and the like and a compound having a hydroxy group or an amino group such as phenol, 4-methoxy phenol, dimethyl phenol, hydroquinone, bisphenol A, naphthols, pyrogallol, polyhydroxy benzophenone, pyrocatechol, pyrogallol monomethyl ether and pyrogallol-1,3-dimethyl ether as well as aniline and 4-amino diphenylamine.

It is further optional according to need that the photosensitive resin composition of the invention is admixed with other known photosensitizing compounds such as mercaptooxazole, mercaptobenzoxazole, mercaptooxazoline, mercaptobenzoazole, benzoxazolinone, benzothiazole, mercaptobenzimidazole, urazole, thiouracil, mercaptopyrimidine and imidazolone as well as derivatives thereof. When used, the amount of these auxiliary photosensitizing compounds in the inventive composition should be in the range from 0.1 to 30 parts by weight or, preferably, from 0.5 to 25 parts by weight per 100 parts by weight of the total amount of the component (a), component (b) and, if used, component (c). When the amount thereof is too small, no substantial further improvement can be obtained in the photosensitivity of the composition while no further improvement can be obtained in the sensitivity of the composition even by increasing the amount thereof to exceed the above mentioned upper limit rather with an economical disadvantage.

The photosensitive resin composition of the invention is used preferably in the form of a solution prepared by dissolving the above described essential and optional ingredients in a suitable organic solvent. Examples of suitable organic solvents include ketones such as acetone, methyl ethyl ketone, cyclohexanone, methyl isoamyl ketone and the like, polyhydric alcohols and derivatives thereof such as monomethyl, monoethyl, monopropyl, monobutyl and monophenyl ethers of ethyleneglycol, ethyleneglycol monoacetate, diethyleneglycol, diethyleneglycol monoacetate, propyleneglycol, propyleneglycol monoacetate, dipropyleneglycol or dipropyleneglycol monoacetate and the like, cyclic ethers such as dioxane and the like, and esters such as methyl lactate, ethyl lactate, methyl acetate, ethyl acetate, butyl acetate and the like. These organic solvents can be used either singly or as a mixture of two kinds or more according to need.

Other optional additives, which have compatibility with and can be added to the inventive composition according to need, include auxiliary resins, plasticizers and stabilizers to improve the properties of the resist layer, coloring agents to increase the visibility of the patterned resist layer formed by development and so on among the additives conventionally used in photosensitive resin compositions.

The procedure for the preparation of a patterned resist layer by using the inventive photosensitive resin composition can be conventional. For example, a substrate such as a semiconductor silicon wafer is evenly coated with the inventive resin composition in the form of a solution by using a suitable coating machine such as a spinner followed by drying to form a resist layer which is exposed pattern-wise to actinic rays such as ultraviolet light emitted from low-pressure, high-pressure and ultra-high-pressure mercury lamps, arc lamps, xenon lamps and the like through a photomask bearing a desired pattern on a minifying light-projection exposure apparatus and electron beams scanned in accordance with a desired pattern to build up a latent image of the pattern in the resist layer. Thereafter, the latent image in the resist layer is developed by a development treatment using a weakly alkaline developer solution such as an aqueous solution of tetramethyl ammonium hydroxide in a concentration of 1 to 10% by weight to give a patterned resist layer having good fidelity to the pattern of the photomask.

In the following, the alkali-developable positive-working photosensitive resin composition of the invention is illustrated in more detail by way of examples but the scope of the present invention is never limited to these examples. In the following examples, the photosensitive resin compositions were evaluated for the items indicated below by the procedures described there.

1. Sensitivity

A semiconductor silicon wafer was evenly coated with the photosensitive resin composition in the form of a solution by using a spinner followed by drying at 100° C. for 90 seconds on a hot plate to give a uniform resist layer having a thickness of 1.3 $\mu$m. The resist layer was then exposed patternwise through a test chart photomask on a minifying light-projection exposure apparatus (Model NSR-1755i7A, manufactured by Nikon Co.) for a length of exposure time varied stepwise by 0.1 second to 0.02 second differences followed by a development treatment for 1 minute at 23° C. with an aqueous solution of tetramethyl ammonium hydroxide in a concentration of 2.38% by weight, rinse in running water for 30 seconds and drying to give a patterned resist layer. The minimum exposure time for obtaining an acceptable patterned resist layer was recorded and taken as a measure of the sensitivity.

2. Heat resistance

The line-and-space patterned resist layer of 1.0 $\mu$m width on a silicon wafer formed in the above described manner was heated for 5 minutes on a hot plate kept at 130° C., 140° C. or 150° C. and the resist layer was microscopically examined to detect deformation of the pattern. The results were recorded as "good" when substantially no deformation was found at the boundary portion between the substrate surface and the line-patterned resist layer to meet the practical requirement for the heat resistance and "poor" when flowing deformation was found in the boundary portion between the substrate surface and the patterned resist layer not to meet the practical requirement.

3. Resolution

The critical resolution in $\mu$m was recorded when the exposure dose was sufficient to reproduce a line pattern of 1.0 $\mu$m line width.

4. Focusing latitude

Recording was made of the depth of focus by which a line-and-space test chart pattern of 0.5 $\mu$m width could be reproduced. The focusing latitude is good to be suitable for practical use when this value is large and poor when this value is small not to meet the requirement for practical use.

Preparation Example 1

A reaction mixture was prepared by dissolving 425 g of 1-[1-(4-hydroxyphenyl) isopropyl]-4-[1,1-bis(4-hydroxyphenyl) ethyl] benzene and 807 g of naphthoquinone-1,2-diazide-5-sulfonyl chloride in 4200 g of dimethyl acetamide and then a mixture of 350 g of triethylamine and 1400 g of dimethyl acetamide was added dropwise to the reaction mixture under vigorous agitation over a period of about 45 minutes. The temperature of the reaction mixture was 18° C. at the start of the reaction and kept not to exceed 35° C. throughout the reaction time.

After completion of the dropwise addition of the triethylamine solution, the reaction mixture was further agitated for additional 75 minutes followed by filtration and the filtrate was admixed with 25 g of 35% hydrochloric acid to precipitate the reaction product, which was collected by filtration, thoroughly washed with deionized water, dehydrated and dried.

The reaction product thus obtained was subjected to the GPC analysis to give a result that the content of the triester, i.e. the full esterification product, was almost 100%.

Preparation Example 2

The procedure of the synthetic reaction was substantially the same as in Preparation Example 1 described above except that the reaction mixture was prepared by dissolving 425 g of 1-[1-(4-hydroxyphenyl) isopropyl]-4-[1,1-bis(4-hydroxyphenyl) ethyl] benzene and 150 g of naphthoquinone-1,2-diazide-5-sulfonyl chloride in 2000 g of dimethyl acetamide and a mixture of 120 g of triethylamine and 700 g of dimethyl acetamide was added dropwise to this reaction mixture under agitation taking 45 minutes.

The reaction product was subjected to the GPC analysis to give a result that the contents of the triester, diester, monoester and unreacted starting reactant were 13%, 42%, 40% and 5%, respectively.

Preparation Example 3

Into a solution of 400 g of a reaction product obtained by the condensation reaction of phenol and salicylaldehyde in the presence of an acidic catalyst having a weight-average molecular weight of 680 and a degree of dispersion of 1.32 (Resin-X T3, a product by Mitsubishi Petrochemical Co.) and 800 g of naphthoquinone-1,2-diazide-5-sulfonyl chloride dissolved in 4000 g of dioxane was added dropwise a mixture of 800 g of triethylamine and 2000 g of dioxane under vigorous agitation taking 45 minutes at room temperature. After completion of the dropwise addition of the triethylamine solution, agitation was continued for further 75 minutes followed by filtration of the reaction mixture to remove the precipitates. The filtrate was admixed with 25 g of 35% hydrochloric acid to precipitate the reaction product which was collected by filtration, washed with deionized water, dehydrated and dried.

Preparation Example 4

A reaction mixture was prepared by dissolving 9.8 g of 2,3,4,4'-tetrahydroxy benzophenone and 26.3 g of naphtho-quinone-1,2-diazide-5-sulfonyl chloride in 340 g of dioxane and 24 g of a 25% by weight aqueous solution of sodium carbonate were added thereto dropwise under vigorous agitation over a period of about 45 minutes. Thereafter, this reaction mixture was admixed with a diluted hydrochloric acid prepared by diluting 25 g of 35% hydrochloric acid with 1000 g of deionized water to precipitate the reaction product, which was collected by filtration, thoroughly washed with deionized water, dehydrated and dried.

Preparation Example 5

The procedure was substantially the same as in Preparation Example 3 described above excepting replacement of 400 g of the commercial product Resin-X T3 with 315 g of a reaction product, which had a weight-average molecular weight of 500 and a degree of dispersion of 1.30, obtained by the condensation reaction of phenol and salicylaldehyde in the presence of an acidic catalyst and decrease of the amount of naphthoquinone-1,2-diazide-5-sulfonyl chloride from 800 g to 567 g.

Preparation Example 6

The procedure was substantially the same as in Preparation Example 3 described above excepting replacement of 400 g of the commercial product Resin-X T3 with 819 g of another condensation reaction product of phenol and salicylaldehyde, which had a weight-average molecular weight of 1300 and a degree of dispersion of 1.38, and increase of the amount of naphthoquinone-1,2-diazide-5-sulfonyl chloride from 800 g to 1476 g.

Example 1

A positive-working photoresist composition was prepared by dissolving 5 g of the dried reaction product obtained in the above described Preparation Example 3 and 20 g of a cresol novolac resin having a weight-average molecular weight of about 7000 in 75 g of ethyleneglycol monoethyl ether acetate followed by filtration.

This photoresist composition was subjected to the evaluation tests for the sensitivity, heat resistance, resolution and focusing latitude to give the results shown in Table 1.

Example 2

The formulation of the positive-working photoresist composition was just the same as in Example 1 excepting replacement of 5 g of the reaction product obtained in Preparation Example 3 with a combination of 1.5 g and 3.5 g of the reaction products obtained in Preparation Examples 1 and 3, respectively. The results of the evaluation tests of this photosensitive resin composition are shown in Table 1.

Example 3

The formulation of the positive-working photoresist composition was just the same as in Example 1 excepting replacement of 5 g of the reaction product obtained in Preparation Example 3 with a combination of each 2.5 g of the reaction products obtained in Preparation Examples 1 and 3. The results of the evaluation tests of this photosensitive resin composition are shown in Table 1.

Example 4

The formulation of the positive-working photoresist composition was just the same as in Example 1 excepting replacement of 5 g of the reaction product obtained in Preparation Example 3 with a combination of 3.5 g and 1.5 g of the reaction products obtained in Preparation Examples 1 and 3, respectively. The results of the evaluation tests this photosensitive resin composition are shown in Table 1.

Example 5

The formulation of the positive-working photoresist composition was just the same as in Example 1 excepting replacement of 5 g of the reaction product obtained in Preparation Example 3 with a combination of each 2.5 g of the reaction products obtained in Preparation Examples 2 and 3. The results of the evaluation tests of this photosensitive resin composition are shown in Table 1.

Example 6

The formulation of the positive-working photoresist composition was just the same as in Example 1 excepting replacement of 5 g of the reaction product obtained in Preparation Example 3 with the same amount of the dried reaction product obtained in Preparation Example 5 described above. The results of the evaluation tests of this photosensitive resin composition are shown in Table 1.

Example 7

The formulation of the positive-working photoresist composition was just the same as in Example 1 excepting replacement of 5 g of the reaction product obtained in Preparation Example 3 with a combination of 1.5 g and 3.5 g of the reaction products obtained in Preparation Examples 1 and 5, respectively. The results of the evaluation tests of this photosensitive resin composition are shown in Table 1.

Example 8

The formulation of the positive-working photoresist composition was just the same as in Example 1 excepting replacement of 5 g of the reaction product obtained in Preparation Example 3 with the same amount of the dried reaction product obtained in Preparation Example 6 described above. The results of the evaluation tests of this photosensitive resin composition are shown in Table 1.

Example 9

The formulation of the positive-working photoresist composition was just the same as in Example 1 excepting replacement of 5 g of the reaction product obtained in Preparation Example 3 with a combination of 1.5 g and 3.5 g of the reaction products obtained in Preparation Examples 2 and 6, respectively. The results of the evaluation tests of this photosensitive resin composition are shown in Table 1.

Comparative Example 1

The formulation of the positive-working photoresist composition was just the same as in Example 1 excepting replacement of 5 g of the reaction product obtained in Preparation Example 3 with the same amount of the reaction product obtained in Preparation Example 4. The results of the evaluation tests of this photosensitive resin composition are shown in Table 1.

Comparative Example 2

The formulation of the positive-working photoresist composition was just the same as in Example 1 excepting replacement of 5 g of the reaction product obtained in Preparation Example 3 with the same amount of the reaction product obtained in Preparation Example 1. The results of the evaluation tests of this photosensitive resin composition are shown in Table 1.

TABLE 1

| | Sensitivity, ms | Heat resistance, °C. 130 | 140 | 150 | Resolution, μm | Focusing latitude, μm |
|---|---|---|---|---|---|---|
| Example 1 | 180 | good | good | good | 0.45 | 1.7 |
| Example 2 | 220 | good | good | good | 0.40 | 1.9 |
| Example 3 | 240 | good | good | good | 0.38 | 2.1 |
| Example 4 | 260 | good | good | good | 0.35 | 2.2 |
| Example 5 | 250 | good | good | good | 0.35 | 2.0 |
| Example 6 | 100 | good | good | good | 0.48 | 1.5 |
| Example 7 | 180 | good | good | poor | 0.45 | 1.7 |
| Example 8 | 200 | good | good | good | 0.35 | 1.9 |
| Example 9 | 280 | good | good | good | 0.35 | 2.0 |
| Comparative Example 1 | 250 | good | poor | poor | 0.45 | 1.5 |
| Comparative Example 2 | 400 | poor | poor | poor | 0.35 | 1.0 |

What is claimed is:

1. An alkali-developable positive-working photosensitive resin composition which comprises, as a uniform blend:
   (a) an alkali-soluble novolac resin;
   (b) a 1,2-quinone diazide sulfonic acid ester of a condensation product having a weight-average molecular weight in the range from 400 to 2000 obtained by the condensation reaction between phenol and a hydroxybenzaldehyde in the presence of an acidic catalyst; and
   (c) an aromatic compound represented by the general formula

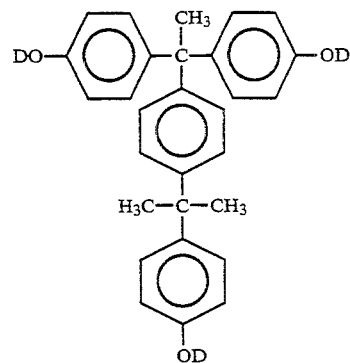

in which at least one of the groups denoted by D is a naphthoquinone-1,2,-diazide-sulfonyl group, the remainder, if any, of the groups denoted by D being each a hydrogen atom.

2. The alkali-developable positive-working photosensitive resin composition as claimed in claim 1 in which the hydroxybenzaladehyde is o-hydroxybenzaldehyde.

3. The alkali-developable positive-working photosensitive resin composition as claimed in claim 1 in which the amount of the component (b) is in the range from 5 to 200 parts by weight per 100 parts by weight of the component (a).

4. The alkali-developable positive-working photosensitive resin composition as claimed in claim 1 in which the total amount of the components (b) and (c) is in the range from 5 to 200 parts by weight per 100 parts by weight of the component (a) and the weight proportion of the component (c) to the component (b) is in the range from 1:10 to 10:1.

5. The alkali-developable positive-working photosensitive resin composition as claimed in claim 1 in which the alkali-soluble novolac resin has a weight-average molecular weight in the range from 2000 to 20000.

6. The alkali-developable positive-working photosensitive resin composition as claimed in claim 1 in which the naphthoquinone-1,2-diazide-sulfonyl group denoted by D in the component (c) is a naphthoquinone-1,2-diazide-4-sulfonyl group or naphthoquinone-1,2-diazide-5-sulfonyl group.

7. The alkali-developable positive-working photosensitive resin composition as claimed in claim 4 in which the total amount of the components (b) and (c) is in the range from 5 to 200 parts by weight per 100 parts by weight of the component (a) and the weight proportion of the component (c) to the component (b) is in the range from 3:7 to 7:3.

* * * * *